US00PP14040P29

(12) United States Plant Patent
van Eijk-Bos et al.

(10) Patent No.: US PP14,040 P2
(45) Date of Patent: Aug. 5, 2003

(54) HOSTA PLANT NAMED 'TWILIGHT'

(76) Inventors: Gerrit van Eijk-Bos, Vitro Westland B.V. Haantje 17-c, Rijswijk ZH 2288 CV (NL); Dirk van Erven, Haantje 17-c, Rijswijk (NL)

( * ) Notice: Subject to any disclaimer, the term of this patent is extended or adjusted under 35 U.S.C. 154(b) by 0 days.

(21) Appl. No.: 08/950,145

(22) Filed: Oct. 14, 1997

(51) Int. Cl.[7] ..... A01H 5/00
(52) U.S. Cl. ..... Plt./68.1
(58) Field of Search ..... Plt./68.1

*Primary Examiner*—Elizabeth C. Kemmerer

(57) ABSTRACT

A mutation selection of Hosta 'Fortunei Auereomarginata' with a wide gold margin and heavy substance.

4 Drawing Sheets

SUMMARY OF THE INVENTION

The new and distinct variety is a tissue culture derived sport of the cultivar Hosta 'Fortunei Aureomarginata'. The plant was discovered by Gerrit van Eijk Bos and Dirk van Erven on the premises of a nursery in Rijswijk, Netherlands. The plant, Hosta 'Twilight', with its unique wide yellow leaf margin, has been reproduced in a stable periclinal variegated form. The new cultivar is hereby named Hosta 'Twilight', and will be sold under that name.

The new cultivar has been asexually propagated via tissue culture techniques at a nursery in Rijswijk, Netherlands. It has also been reproduced through normal division of the rhizome. Although tissue culture, or micropropagation can produce aberrants or mutants requiring some culling, to one skilled in the art of tissue culture, it can be a propagation tool capable of producing clones of identical plants.

Through the development and improvement of the tissue culture process at a nursery in Rijswijk, Netherlands, Hosta 'Twilight' has been successfully reproduced proliferating plants that are substantially identical to the original plant.

BRIEF DESCRIPTION OF THE DRAWINGS

The invention is illustrated in the attached four (4) photographic drawings in which.

DETAILED DESCRIPTION OF PREFERRED EMBODIMENT

Figure 1:
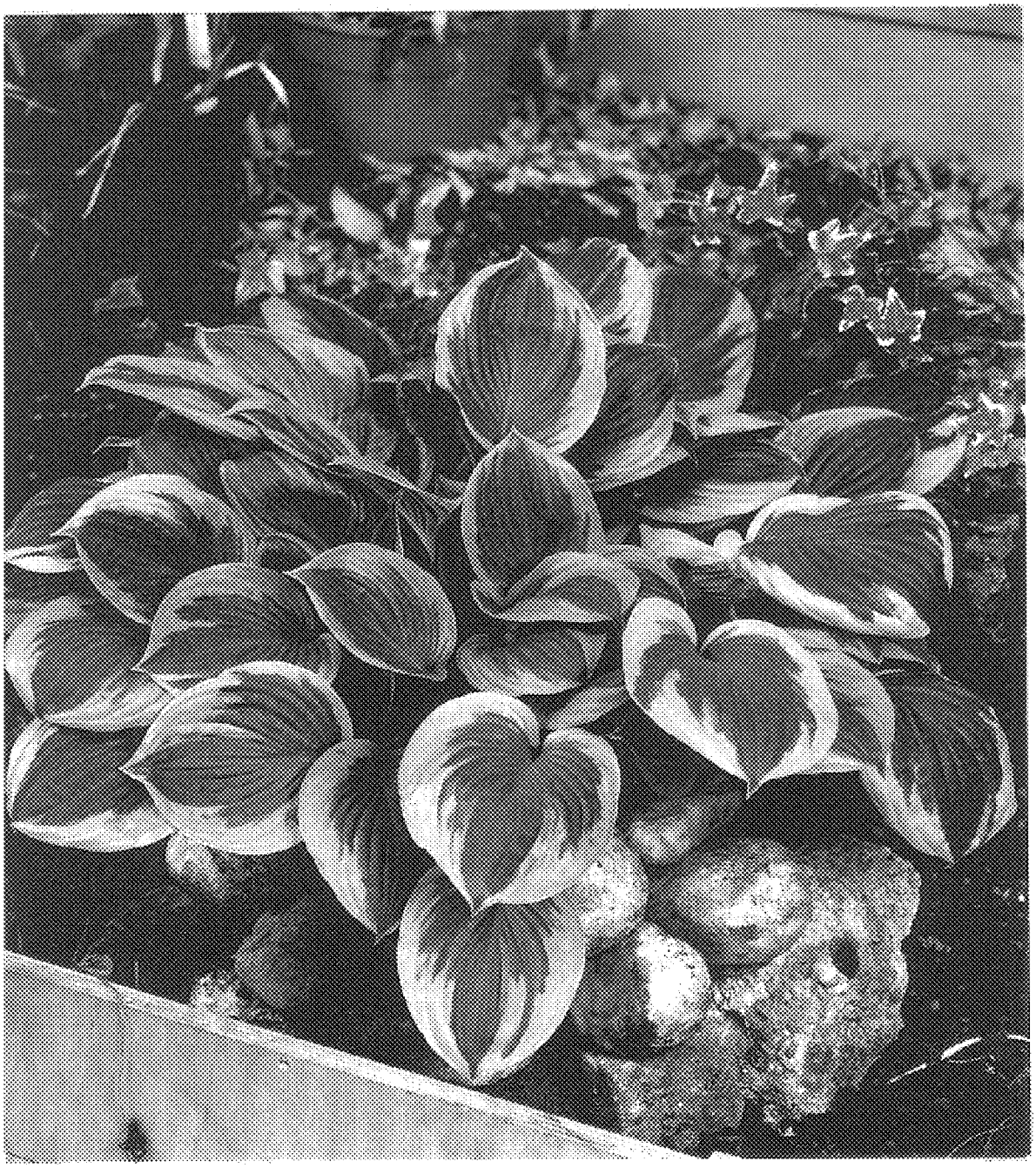
FIG. 1 shows the plant as a clump growing in a garden environment.
Figure 2:
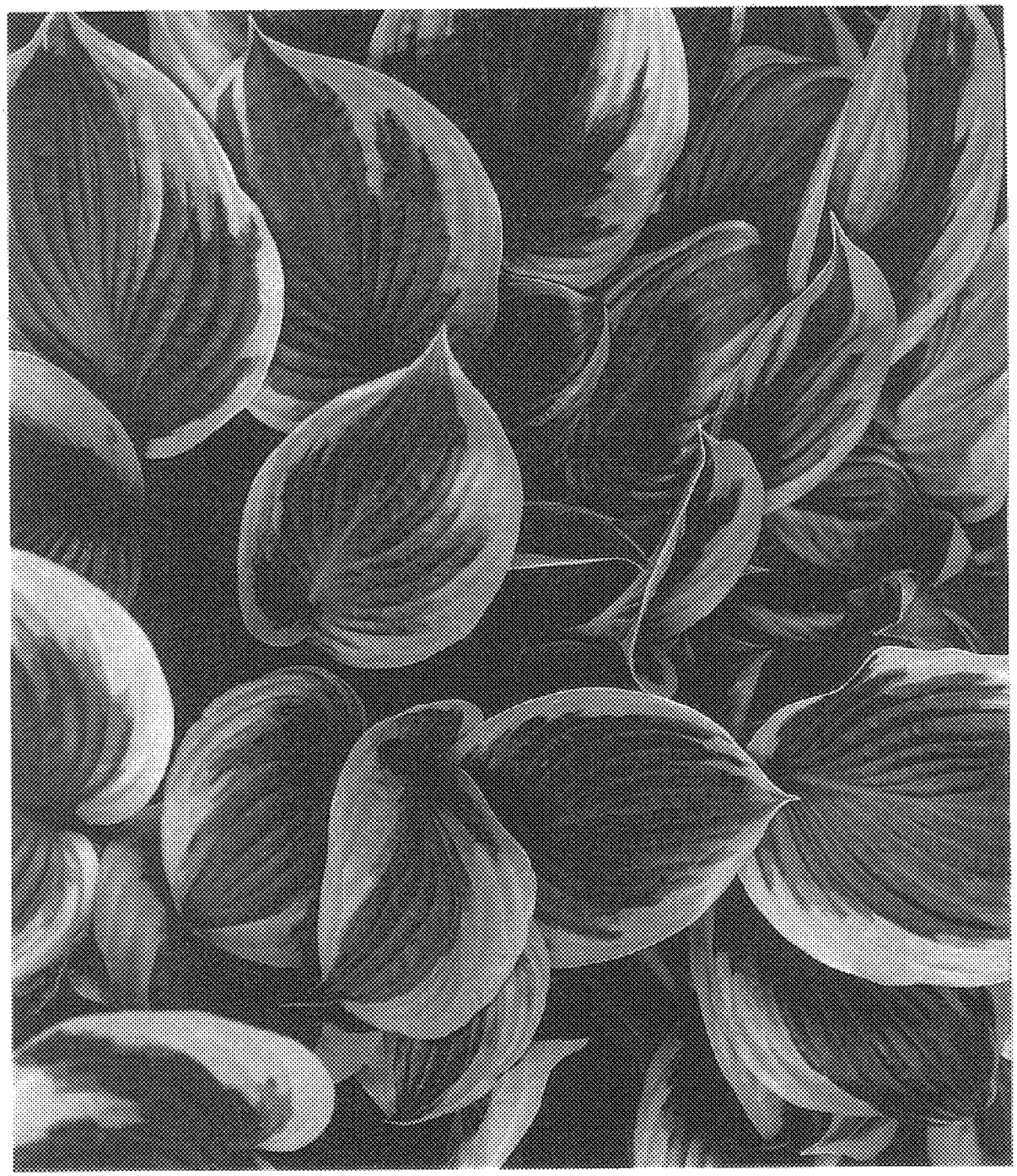
FIG. 2 shows the plant with a close-up of the leaves showing the very early spring color of the foliage and the beginning of the color change process.
Figure 3:
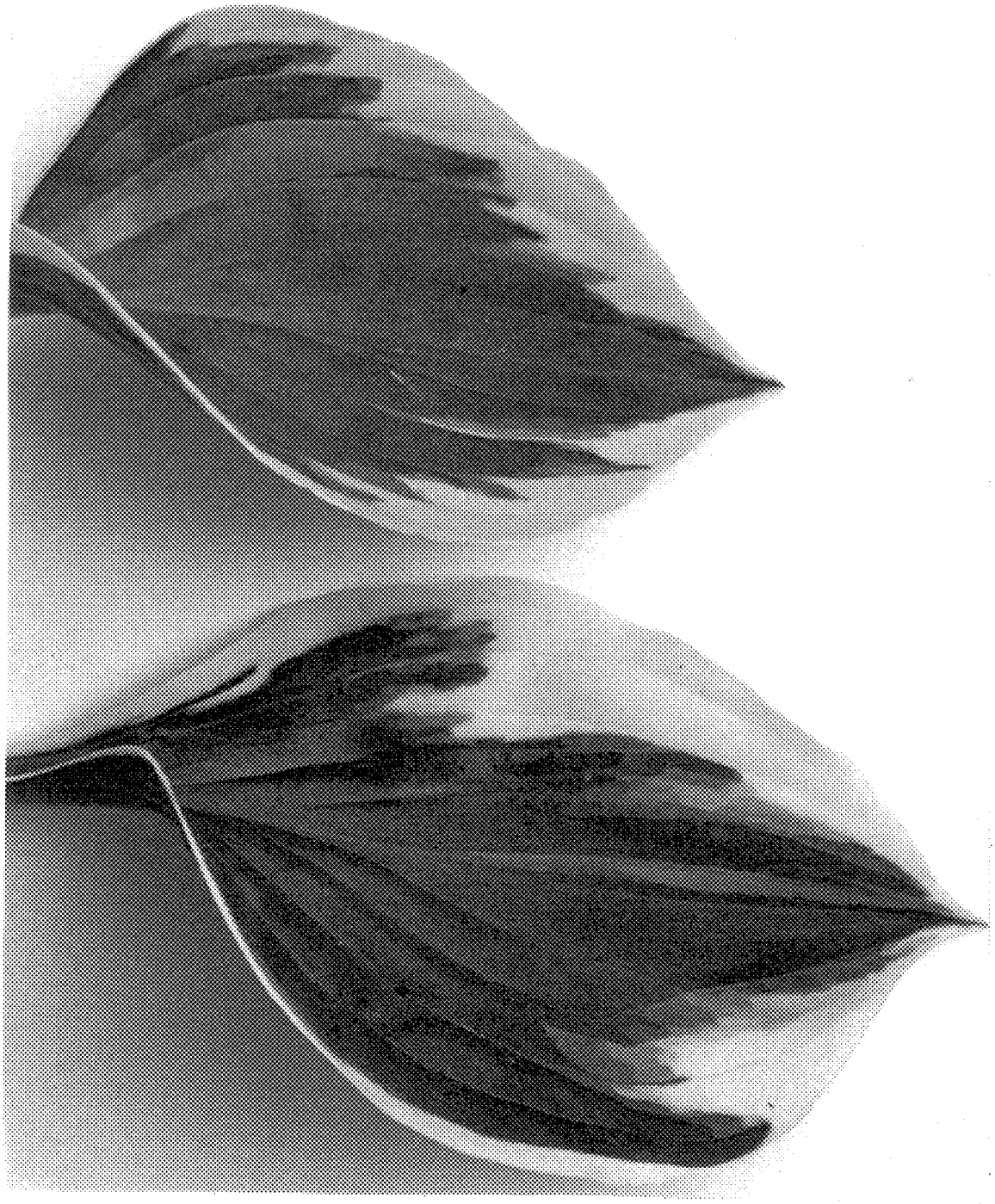
FIG. 3 shows the plant with a close-up of the leaves showing the foliage comparison between young early growth and older growth that has been more exposed to sunlight.
Figure 4:
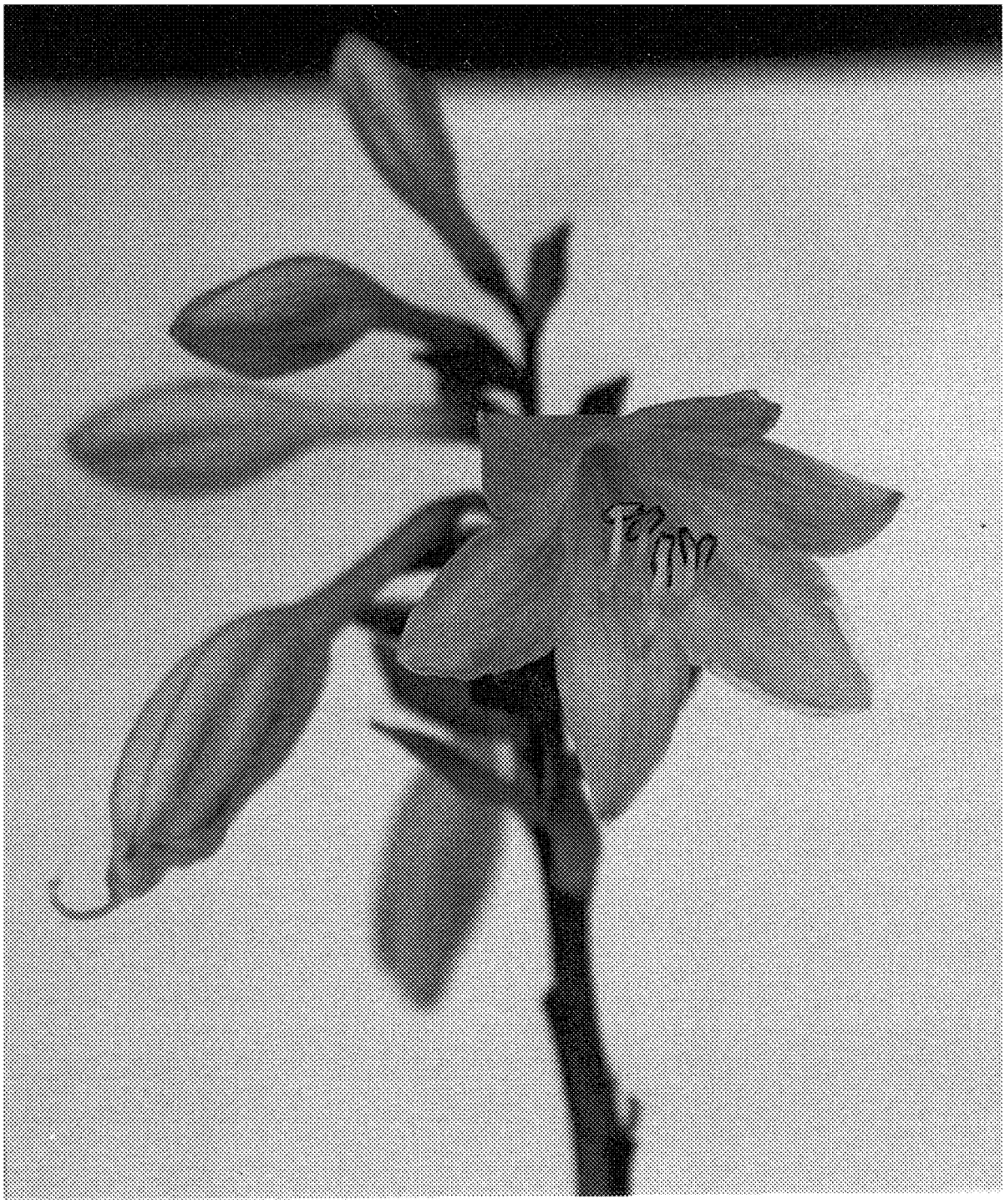
FIG. 4 shows the plant stem with flowers in bud and open flower state.

The genus Hosta is a diverse and complicated compilation of hybrids, species and sports as noted in *The Genus Hosta* by W. George Schmid. The frequency to mutate and produce variegated individuals is much higher than the average plant. Hosta 'Twilight' is the product of such a mutation. It was in the process of tissue culture propagating the plant, Hosta 'Fortunei Aureomarginata', that a variant was discovered.

Hostas are herbaceous, rhizomatous perennials with a group of basal leaves tufted around a short subterranean stem. The flowers are generally held up on capitate racemes or rarely panicles. Foliage tends to still be the characteristic of highest ornamental value. The size of mature hosta plant foliage varies from two (2) inches to over forty (40) inches high, and three (3) inches to ten (10) feet wide. Foliage color varies from yellow, chartreuse, light green, medium green, deep green, and glaucous forms of blue and blue-green, to variegations containing white and creamy white and all the other color combinations.

Hosta 'Fortunei Aureomarginata' has a medium green leaf with a gold margin. The margin lightens as the growing season progresses depending on the amount of direct or indirect sunlight, as with the amount of heat received by the plant while growing. Flowering is from July 25 to August 15 on unbranched panicles or scapes ranging from thirty (30) to forty (40) inches tall, and displaying twenty-five (25) to forty (40) flowers. Flowering is usually more prolific in plenty of light and ideal growing conditions. The flowers are tubular shaped with the normal six tepals of medium lavender color and showing striping of a deeper lavender color in the center of each petal with white on the outside edge of each petal.

The new cultivar is unique from the sport parent in that it has much wider margins, a darker green center and a more rigid leaf. The margin of Hosta 'Twilight' is nearly twice the width of Hosta 'Fortunei Aureomarginata'. It has the same basic color pattern of the margin. The leaf center is much darker green. The leaves of Hosta 'Twilight' are more rugose or stiff, and more glossy on the upper surface than 'Fortunei Aureomarginata'. 'Fortunei Aureomarginata' has a dull and lightly glaucous upper surface. 'Twilight' has the same glaucous under side of the leaf. Because of the heavier form of the leaves the overall habit tends to be more stiff and upright.

Using The Royal Horticultural Colour Chart, 1995 edition, the plant as grown in Rijswijk, Netherlands, is described as follows: The new variety has leaves with a center color of RHS 136A. When fully mature the leaf center becomes the color of RHS 137 B. At the beginning of the season the leaf edge or margin is RHS 145 A. During the season the margin lightens with the exposure to sun and heat from a 150 C to 145 D. In higher light levels the leaf center becomes a yellow-green 146 A, and the margin lightens to a white 155A. This color change occurs more rapidly with higher light intensities and longer exposures to higher light levels, and with an increase in temperature. Higher temperatures speed up the lightening of the leaf margin. The color of the leaves may vary with temperature, light exposure, and nutrients as well as other growing conditions. The flowers of the new cultivar are identical to Hosta 'Fortunei Aureomarginata'. It starts out as RHS 85 C and becomes RHS 85 D. The flower stem is RHS 144 C and reaches 90 cm. The leaf dimensions measure 20 cm in length and 14 cm in width. The plant clump measures 60 cm in diameter and 40 cm in height. These measurement may be larger or smaller depending on age of the clump, fertility and other growing conditions.

The new cultivar, Hosta 'Twilight', is unique from the parent and every other hosta in a rather unusual way. It has heavier substanced, more rugose leaves, similar to the resulting mutation producing Hosta 'Gold Margin', U.S. Plant Pat. No. 8,016, by Clarence H. Falstad, III. It also has a variegated margin that covers nearly twice as much of the leaf surface as the original sport parent, Hosta 'Fortunei Aureomarginata'. The margin is made from cells of what is commonly, in monocots, referred to as the L-1 histogenic layer. This is the region comprising the outer layer of the meristem and must have been affected in the mutation. Hosta 'Twilight' has a shinier upper surface to the leaf than the original cultivar.

The flowers of Hosta 'Twilight' are essentially identical to those of 'Fortunei Aureomarginata'. The buds are a violet 85 D and 85 A, and the opened flowers have tepals of Red purple 69D and violet stripes of 84 B. The anthers are about RHS 83 A.

The new hosta variety is hardy to at least -35° Celsius. As with other hostas, it does die back to the ground with frost or freezing conditions either in late spring or in the fall. It can grow in almost any type of soil conditions, and is drought tolerant for brief periods. However, it grows much better with copious amounts of water and good drainage. The plant is resistant to most major diseases and pests, but under high humidity some lush growth may be partially consumed by slugs or snails.

We claim:

1. The new and distinct cultivar, named Hosta 'Twilight' substantially herein described and shown with a wide yellow margin, shiny leaf surface, and more rugose substance, and suitable for landscape use or container growing.

* * * * *